(12) United States Patent
Chudzinski-Tavassi et al.

(10) Patent No.: US 8,673,840 B2
(45) Date of Patent: Mar. 18, 2014

(54) METHODS FOR GROWING TISSUE WITH LOPAP-BASED PHARMACEUTICAL COMPOSITIONS

(75) Inventors: Ana Marisa Chudzinski-Tavassi, São Paulo (BR); Marcio Falci, São Paulo (BR); Cleyson Valenca Reis, São Paulo (BR); Durvanei Augusto Maria, São Paulo (BR)

(73) Assignees: Biolabs Sanus Farmaceutica Ltda., Sao Paulo (BR); Fundacao de Amparao a Pesquisa do Estado de Sao Paulo-Fapesp, Sao Paulo (BR); Ana Marisa Chudzunski-Tavassi, Sao Paulo (BR)

( * ) Notice: Subject to any disclaimer, the term of this patent is extended or adjusted under 35 U.S.C. 154(b) by 905 days.

(21) Appl. No.: 12/066,192

(22) PCT Filed: Sep. 8, 2006

(86) PCT No.: PCT/BR2006/000180
§ 371 (c)(1),
(2), (4) Date: Jan. 20, 2009

(87) PCT Pub. No.: WO2007/028223
PCT Pub. Date: Mar. 15, 2007

(65) Prior Publication Data
US 2009/0170182 A1    Jul. 2, 2009

(30) Foreign Application Priority Data
Sep. 8, 2005  (BR) ................................. 0504199

(51) Int. Cl.
*A61K 38/00* (2006.01)

(52) U.S. Cl.
USPC ............................................. 514/1.1

(58) Field of Classification Search
None
See application file for complete search history.

(56) References Cited

U.S. PATENT DOCUMENTS

| 2004/0084867 A1 | 5/2004 | Leyland-Jones |
| 2005/0069877 A1 | 3/2005 | Gandhi et al. |

FOREIGN PATENT DOCUMENTS

| BR | PI0200269 | 6/2004 |
| BR | PI0403882 | 5/2006 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Chudzinski-Tavassi et al, Exploring new molecules and activities from *Lonomia obliqua* caterpillars. Pathophysiol Haemost Thromb. 2005;34(4-5):228-33.*
Reis et al, In vivo characterization of Lopap, a prothrombin activator serine protease from the *Lonomia obliqua* caterpillar venom. Thromb Res. Jun. 1, 2001;102(5):437-43.*
Maranga et al, Enhancement of Sf-9 cell growth and longevity through supplementation of culture medium with hemolymph. Biotechnol Prog. Jan.-Feb. 2003;19(1):58-63.*
Merriam-Webster definition of "Tissue". Downloaded Jul. 26, 2012.*
Chudzinski-Tavassi et al., "Effects of lopap on human endothelial cells and platelets," *Haemostasis* 31:257-265 (2001).
Donato et al., "*Lonomia oblique* caterpillar spicules trigger human blood coagulation via activation of factor X and prothrombin," *Thromb. Haemost.* 79:539-542 (1998).
Flower et al., "The lipocalin protein family: structural and sequence overview," *Biochim. Biophys. Acta* 1482:9-24 (2000).
Fritzen et al., "A prothrombin activator (Lopap) modulating inflammation, coagulationand cellsurvival mechanisms," *Biochem. Biophys. Res. Comm.* 333(2):517-523 (2005).
Kelen et al., "Hemorrhagic Syndrome Induced by Contact with Caterpillars of the Genus *Lonomia* (Saturniidae, Hemileucinae)," *J. Toxicol.-Toxin Rev.* 14:283-308 (1995).
Lorini et al., "Aspectos Morfologicos de *Lonomia oblique* Walker (Lepidoptera: Saturniidae)," *Neotropical Entomology* 30(3): 373-378, 2001, Abstract only.
Prezoto et al., "Antithrombotic effect of *Lonomia oblique* caterpillar bristle extract on experimental venous thrombosis," *Braz. J. Med. Biol. Res.* 35(6):703-712 (2002).
Reis et al., "A Ca++ activated serine protease (LOPAP) could be responsible for the haemorrhagic syndrome caused by the caterpillar *Lonomia oblique*. L oblique Prothrombin Activator Protease," *Lancet* 353:1942 (1999).
Reis et al., "A prothrombin activator serine protease from the *Lonomia oblique* caterpillar venom (Lopap) biochemical characterization," *Thromb. Res.* 102:427-436 (2001).
Reis et al., "In vivo characterization of Lopap, a prothrombin activator serine protease from the *Lonomia oblique* caterpillar venom," *Thromb. Res.* 102:437-443 (2001).
Souza et al., "Purification and characterization of an anti-apoptotic protein isolated from *Lonomia oblique* hemolymph," *Biotechnol. Prog.* 21:99-105 (2005).
Zannin et al., "Blood coagulation and fibrinolytic factors in 105 patients with hemorrhagic syndrome caused by accidental contact with *Lonomia oblique* caterpillar in Santa Catarina, southern Brazil," *Thromb. Haemost.* 89:355-364 (2003).
Written Opinion; Application No. PCT/BR2006/000180; mailed Feb. 1, 2007; Applicant: Biolab Sanus Farmaceutica LTDA., 6 pages.

* cited by examiner

*Primary Examiner* — Sheridan Swope
(74) *Attorney, Agent, or Firm* — Fish & Richardson P.C.

(57) ABSTRACT

The invention refers to pharmaceutical compositions and cosmetic compositions comprising a prophylactic or therapeutically effective quantity of at least one polypeptide substantially identical to Lopap (a lipocalin-related protein with prothrombin activating protease activity). The invention refers to the use of these compositions as modulators of cell death and anti-aging agents.

3 Claims, 12 Drawing Sheets

SEQUENCE LISTING

```
<160> NUMBER OF SEQ ID NOS: 9

<210> SEQ ID NO 1
<211> LENGTH: 187
<212> TYPE: PRT
<213> ORGANISM: Lonomia oblique

<400> SEQUENCE: 1

Gly Ser Asp Val Val Ile Asp Gly Ala Cys Pro Asp Met Lys Ala Val
 1               5                  10                  15

Ser Lys Phe Asp Met Asn Ala Tyr Gln Gly Thr Trp Tyr Glu Ile Lys
            20                  25                  30

Lys Phe Pro Val Ala Asn Glu Ala Asn Gly Asp Cys Gly Ser Val Glu
        35                  40                  45

Tyr Thr Pro Asp Asn Gly Leu Leu Lys Val Arg Ala Gly His Val Glu
    50                  55                  60

Asp Asp Ile Glu Lys Phe Val Val Gly Val Leu Thr Lys Asn Ala Asp
65                  70                  75                  80

Thr Ser Asp Ala Glu Leu Thr Leu Ser Val Val Val Gly Asp Tyr Val
                85                  90                  95

Arg Val Ala Pro Leu Trp Ile Leu Ser Thr Asp Tyr Asp Asn Tyr Ala
            100                 105                 110

Ile Gly Tyr Ser Cys Lys Asp Tyr Lys Lys Ser Asn Gln His Arg Val
        115                 120                 125

Asn Ile Trp Ile Leu Ser Arg Thr Lys Thr Leu Asn Glu Ser Ser Lys
    130                 135                 140

Ser Thr Val Asn Lys Phe Leu Lys Glu His Ser Lys Glu Phe Asp Gln
145                 150                 155                 160

Ser Lys Phe Val Glu Thr Asp Phe Ser Glu Lys Ala Cys Phe Phe Lys
                165                 170                 175

Lys Ser His Val Tyr Thr Val Pro Phe Gly Ala
            180                 185

<210> SEQ ID NO 2
<211> LENGTH: 606
<212> TYPE: DNA
<213> ORGANISM: Lonomia oblique
```

-continued

<400> SEQUENCE: 2

```
atgaaattt tgggctttt ccttgcgatt ttggcgtcga ccgcggcgga cgtcgtcata        60
gacggagcgt gtcctgacat gaaggcggta tcgaaatttg acatgaatgc ttatcaagga    120
acgtggtacg agatcaagaa attccccgtg gctaatgaag cgaacggtga ttgtggaagt    180
gttgagtata cccccgacaa tggactactg aaggtgagag cgggacacgt tgaagatgat    240
atcgagaagt ttgttgtcgg agtcctcacc aagaatgcag acaccagcga tgctgagctc    300
actctcagcg ttgtagtcgg cgactacgtc cgcgttgcac cgctgtggat tctttctact    360
gattacgaca actatgctat cggctactcc tgcaaagact acaagaagag caaccaacac    420
agggtaaaca tctggattct ctcgaggacc aagactctca acgaaagttc caagtccact    480
gtcaacaagt tccttaagga gcactcaaag gagttcgatc aatcgaaatt tgtcgagaca    540
gatttctccg aaaaagcatg cttcttcaag aaatcacacg tgtacactgt accattcgga    600
gcttaa                                                               606
```

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3

```
gaggaagtag actgatatta                                                 20
```

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4

```
ccttcccaga ggaaaagcaa                                                 20
```

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5

```
gatggacggg tccggaga                                                   18
```

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6

```
ctcagcccat cttcttccag                                                 20
```

<210> SEQ ID NO 7
<211> LENGTH: 20
<212> TYPE: DNA
<213> ORGANISM: Artificial Sequence
<220> FEATURE:
<223> OTHER INFORMATION: primer

```
<400> SEQUENCE: 7
ggtgaaggtc ggagtcaacg                                                    20

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
tccttggagg ccatgtgggc cct                                                23

<210> SEQ ID NO 9
<211> LENGTH: 13
<212> TYPE: PRT
<213> ORGANISM: Homo sapiens
<220> FEATURE:
<223> OTHER INFORMATION: /note=  covalent linkage to Abz (ortho-
      aminobenzoic acid)
<220> FEATURE:
<223> OTHER INFORMATION: /note=  covalent linkage to EDDnp (N-[2,4]
      ethylenediamine)

<400> SEQUENCE: 9

Tyr Gln Thr Phe Phe Asn Pro Arg Thr Phe Gly Ser Gln
 1               5                  10
```

METHODS FOR GROWING TISSUE WITH LOPAP-BASED PHARMACEUTICAL COMPOSITIONS

FIELD OF THE INVENTION

The invention refers to pharmaceutical compositions based on a prothrombin activating protease (Lopap), including its recombinant form, and its use as a cell death modulator, and as an anti-aging agent.

BACKGROUND OF THE INVENTION

Genus *Lonomia* is known for causing systemic poisoning from the inoculation of its poison through the skin, with consequent hemorrhagic manifestations with variable intensity, bringing the risk of death in some cases (Lorini, L. M., Passo Fundo, Brazil: EDIUPF, 1999, pages 25-35). The species *Lonomia obliqua* (Lemaire, C., *Ann. Soc. Entomol. Fr.* 8: 767-861, 1972) has caused epidemic accidents in areas of Southern Brazil (Ministério da Saúde, Fundação Nacional de Saúde, *Acidentes por Lepidópteros* in: *Manual de diagnóstico e tratamento de acidentes por animais peçonhentos*, Brasilia, 1998, page 131).

Patients who suffered accidents bear, among other symptoms, mainly after a period of 1 to 48 hours, blood dyscrasia (change in the proportion of blood elements), followed or not by hemorrhagical occurrences, which may cause death (Kelen, E. M. A. et al., *J. Toxicol-Toxin Rev.,* 1995; 14: 283-308; Brazil, 1998).

Zannin established coagulation and fibrinolysis standards in plasma of 105 patients, and confirmed that poisoning affects coagulation and fibrinolysis. Their results showed intense coagulopathy consumption, which may be related to poison components in the bristles of caterpillars *Lonomia obliqua*, which have powerful procoagulant action, causing secondary activation of fibrinolysis (Zannin M. et al., *Thromb. Haemost.,* 89: 355-364, 2003).

The extract of bristles of *L. obliqua* is effective for the experimental prevention of vein thrombosis in mice (Prezoto, B. C. et al., *Braz. J. Med. Biol. Res.* 2002; 35 (6): 703-12).

The poison of the caterpillar *L. obliqua* has some components which interfere in the coagulation system. The presence of prothrombin and Factor X activators in the extract of bristles of *L. obliqua* has been detected (Donato, J. L. et al., *Thromb. Haemost.* 1998; 79: 539-42; Kelen et al., 1995).

The authors of the invention have previously isolated and characterized a 69 kDa prothrombin activator protease called Lopap (*Lonomia obliqua* prothrombin activator protease), which has serinoprotease characteristics and procoagulant activity, exhausting blood of fibrinogen (Brazilian patent document PI 0200269). Lopap is structurally different from other prothrombin activators: the N-terminal portion bears 45.6% identity with the N-terminal portion of insecticianine of hemolymph of *Manduca sexta*; and Fragments I, II, III and IV show identity of 36.4%, 37.5%, 42.9% and 55.5%, respectively, with the corresponding internal fragments of insecticianine.

When intraperitoneally injected in mice in high concentrations (>100 µg/kg), Lopap develops thrombi in small veins and arteries, and the migration of polymorphonuclei to lungs and kidneys (Reis, C. V. et al., *Lancet* 1999, 353: 1942; Reis, C. V. et al., *Thromb. Res.* 2001, 102: 437-43; Reis, C. V. et al., *Thromb. Res.,* 2001, 102: 427-436).

Lopap also acts on endothelial cells (HUVECs), as an expression inducer for adhesion molecules such as ICAM-1 and E-selectin, but not VCAM. The non-expression of VCAM suggests that the action of Lopap is not comparable to TNF-α or thrombin on endothelial cells.

The thrombin produced by Lopap is functional and inhibited by Antithrombin III (AT), being able to add platelets, coagulate plasma and fibrinogen, suggesting that this protease is similar to α-thrombin (Chudzinski-Tavassi, A. M. et al., *Haemostasis* 2001; 31: 257-265).

The recombinant form of Lopap is known. The Brazilian patent document PI 0403882 discloses a process to obtain recombinant Lopap (rLopap) in its monomeric form, its amino acid sequence, and its use as a defibrinogenating agent. The sequence of the recombinant protein, on average, presents 35% identity with lipocalin family proteins. Lipocalins are a family of proteins that store and transport hydrophobic and/or chemically sensitive organic compounds.

SUMMARY OF THE INVENTION

The present invention relates to the Lopap protein and nucleic acids, pharmaceutical and cosmetic compositions containing them, and methods of prophylactic and therapeutic treatment. These treatments can be used to modify, ameliorate, reduce, or prevent disorders. More specifically, Lopap can be used to reduce cell death or degeneration, to reduce or repair tissue degeneration, and is useful for the treatment of cell or tissue disorders caused by wounds, disease, aging, and external agents.

The invention is based, in part, on the discovery that Lopap prevents apoptosis and increases cell viability. Accordingly, the invention pertains to a method of treating a disorder associated with loss of cell viability by administering a pharmaceutically effective amount of a composition comprising Lopap. The Lopap protein can be combined with other agents that increase cell viability.

The invention is also based, in part, on the discovery that Lopap increases cell expression of extracellular matrix proteins, which are important for preserving the integrity of tissues, and the cells within the tissues. Accordingly, the invention pertains to a method for treating a disorder associated with the loss of tissue integrity, by administering a pharmaceutically effective amount of Lopap. Lopap can be combined with other agents that preserve integrity of tissues.

Lopap and Lopap compositions can be use to treat disorders associated with cell death, such as bacterial and viral infection (e.g., human immunodeficiency virus); neurological diseases (e.g., Alzheimer's disease, Parkinson's disease, amyotrophic lateral sclerosis (ALS) retinitis pigmentosa, spinal muscular atrophy, and various forms of cerebellar degeneration); hematologic diseases (e.g., anemia associated with chronic disease, aplastic anemia, chronic neutropenia, and myelodysplastic syndromes); inflammatory disorders; myocardial infarctions; stroke; and other disorders associated with cell death or degeneration.

Lopap and Lopap compositions can be use to treat disorders associated with loss of tissue integrity, such as ulcers, asthma, acute respiratory distress syndrome, skin aging, keratoconus, restenosis, osteo- and rheumatoid arthritis, degenerative joint disease, bone disease, wounds, hypovolemic shock, periodontal disease, epidennolysis bullosa, scleritis, atherosclerosis, multiple sclerosis, inflammatory diseases, vascular leakage syndrome, and collagenase induced disease.

In another aspect, Lopap can be used in vivo or in vitro to improve the viability of cells. In vitro uses include cell culture methods to propagate or manipulate cells. Contemplated methods include cell culture for tissue engineering, stem cell work, and industrial work. In a further aspect, Lopap can be used to improve the viability of cells in biotechnology processes, for example, cell methods for the production of molecules (e.g. organic, inorganic, and macromolecule), and cell methods to alter or degrade molecules. In another aspect, Lopap can be used in vivo or in vitro to reduce or repair degeneration of tissues. In vitro uses include culture methods to propagate or manipulate tissues.

In another aspect, the invention refers to methods of treatment of disorders with cell death or degeneration, or tissue degeneration, including administering to a patient a pharmaceutically effective amount of Lopap. In certain embodiments, the disorders are caused by wound, disease, aging, or an external agent. Lopap can be used alone or in a composition, and administered topically, orally, parenterally, nasally, or pulmonary, or by implant that may use a slow-release formulation. Lopap can be administered at about 1 □g/kg/day to 500 mg/kg/day relative to the patient's weight.

In another aspect, the invention includes kits comprising a pharmaceutically effective amount of Lopap or Lopap composition including instructions for use. In another aspect, the invention includes Lopap or Lopap composition for use as medicaments. And in another aspect, the invention encompasses uses of Lopap or Lopap compositions for the manufacture of a medicament.

Unless defined, all technical and scientific terms used herein have the meaning as commonly understood by one of ordinary skill in the art to which this invention belongs. Although methods and materials similar or equivalent to those described herein can be used in the practice or testing of the present invention, suitable methods and materials are described below. All publications, patents and applications, and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE INVENTION

Figure 1:
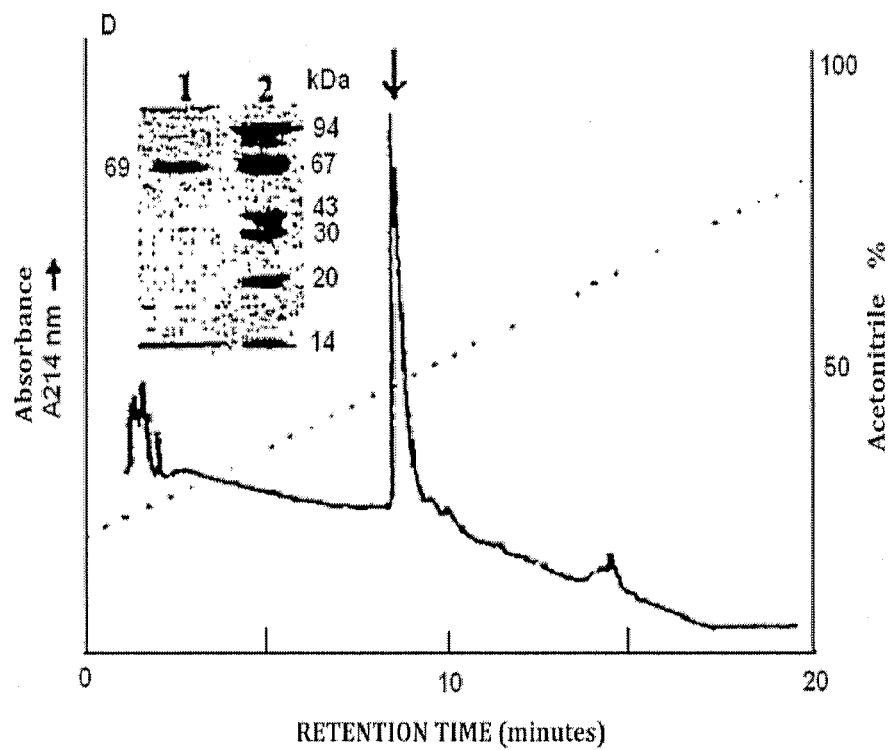
FIG. 1 shows the profile of the protein Lopap, purified by reverse phase chromatography, presenting one single band of 69 kDa molecular weight, determined by means of SDS-PAGE analysis.

The practice of the present invention employs, unless indicated, conventional methods of virology, microbiology, molecular biology, and recombinant DNA techniques within the skill of the art. Such techniques are explained fully in the literature (see, e.g. Sambrook, et al. Molecular Cloning: A Laboratory Manual (Current Edition); DNA Cloning: A Practical Approach, Vol. I & II (D. Glover, ed.), Oligonucleotide Synthesis (N. Gait, ea., Current Edition); Nucleic Acid Hybridization (B. Hames & S. Higgins, eds., Current Edition); Transcription and Translation (B. Hames & S. Higgins, eds., Current Edition); CRC Handbooks).

The invention is based, in part, on the discovery that Lopap prevents apoptosis and increases cell viability. The invention is also based, in part, on the discovery that Lopap increases cell expression of extracellular matrix proteins, which are important for preserving the integrity of tissues, and the cells within the tissues. And the invention is also based, in part, on the discovery that Lopap increases cell expression of factors that regulate muscle relaxation, which is important for preserving the integrity of tissues, and the cells within the tissues.

The methods and compositions of the invention can be used to treat disorders that involve cell death or degeneration, or disorders that involve tissue degeneration. The methods and compositions of the invention can also be used to treat similar disorders occurring in methods to culture or manipulate cells, methods to culture or manipulate tissues, and methods that employ cells to produce, alter, or degrade molecules.

The invention is described in more detail in the following subsections.

1. Cell Death and Degeneration

The poison from the caterpillar *Lonomia oblique* has components with procoagulant action, which causes intense coagulopathy consumption, and hemorrhagic manifestations. Recently, the hemolymph of *Lonomia oblique*, which shares many components with the poison, was also found to be able to promote growth and longevity of Sf-9 cells (Souza, A. P., et al., *Biotechnol. Prog.*; 21: 99-105, 2005). The authors found hemolymph fractions with longevity activity. There was no identification to the reactive agents involved in the longevity activity.

It was determined in this invention that Lopap alone increases the growth and longevity of cells (see Examples). The data demonstrates that Lopap decreases apoptosis and increases viability in HUVECs deprived of serum. The data also demonstrates that Lopap increases expression of the gene Bcl-2 (an anti-apoptotic protein), decreases expression of the gene Bax (a pro-apoptotic protein).

Bcl-2 has been reported to be associated with pathologic cell survival, is expressed at high levels in several leukemias, and leads to tumor progression and resistance to chemotherapy-induced and apoptosis. Bax has been reported to countering these effects: Bax activation leads to cytochrome c release and initiation of the mitochondrial apoptosis program.

It was also determined in this invention that Lopap alone increases the expression of nitric oxide. Nitric oxide has been reported to be an important signaling molecule in mammals and humans. Among many functions, nitric oxide has antioxidant activity, which can contribute to preventing cell death and degeneration, and tissue degeneration.

Methods of reducing cell death or degeneration are also important as methods for reducing or repairing tissue degeneration.

2. Tissue Degeneration

It was determined in this invention that Lopap alone increases expression of proteins important in reducing and repairing tissue degeneration (see Examples). Lopap is able to stimulate expression of at least two groups of molecules important for tissue structure: (1) proteins found in the extracellular matrix; and (2) molecules that regulate muscle relaxation.

The extracellular matrix (ECM) has been reported to be the largest component of the dermal skin layer, and the synthesis of ECM is a key feature of tissue growth and wound healing, especially when there has been a significant loss of tissue. The ECM is composed of three main classes of molecules: (1) fibrous structural proteins (e.g. collagens, fibronectin, and tenascin); (2) elastic fiber proteins (e.g. elastin), and (3) proteoglycans. In addition to serving as scaffold and structural support for cells, the ECM regulates cell adhesion, lubricates cells, and provides a transport system for nutrients and waste.

Collagen contributes 80% of the weight of skin and is responsible for tensile strength and protection against external trauma. Elastic fibers contribute 2% to 4% of the ECM, and provide elasticity to the skin (Uitto, J., *J. Invest. Dermatol.* 72: 1-10, 1979); and (3) proteoglycans, contributing 0.1% to 0.3% of the weight of tissue, support (skin) hydration due to the water-retaining capacity of hyaluronic acid (Davidson, E. A., Polysaccharide structure and metabolism, in: Montagna W. (ed), Aging: Biology of skin, Oxford, Pergamon Press, 1965, pp. 255-270). Processes that alter or degrade these components can result in detrimental clinical manifestations for tissue—especially in tissues that are stretched or compressed (e.g. aorta, lungs, skin, cartilage, and tendons)—such as lack of new tissue growth, atrophy, loss of resilience, and ageing.

New tissue growth and fibrinogenesis is controlled by the balanced synthesis and interaction of the ECM proteins. For example, microfibrils—a component of elastic fibers—are introduced into the extracellular medium by fibroblasts, mesenchymal and other cells, which, with aggregation, form a support structure for the elastic fiber, where elastin is deposited. This basic structure indicates the form and direction of the future elastic fiber; Ross, R., *J. Histochem. Cytochem.*, v. 21, p. 199-208, 1973; Ross, R. et al, *Adv. Exp. Med. Biol.*, v. 79, p. 7-17, 1977).

In acute wounds, the provisional wound matrix, containing fibrin and fibronectin, provides a scaffolding to direct cells into the injury, as well as stimulating them to proliferate, differentiate and synthesise new ECM. Chronic wounds contain increased levels of inflammatory cells, giving rise to proteases that degrade the ECM components, growth factors and receptors essential for healing.

Current approaches in wound healing focus on re-establishing a functional ECM, including methods or products that reduce excessive protease levels or contribute functional ECM proteins, thereby facilitating the healing process. Some of these approaches provide a competitive substrate (collagen) for the proteases and thereby reducing proteolytic destruction of essential ECM components (fibronectin) and platelet-derived growth factors (PDGFs). Other approaches provide unique proteins (amelogenin) to replace corrupted ECM (Schultz, G S, World Wide Wounds, *Extracellular matrix: review of its roles in acute aand chronic wounds*, August 2005).

It was determined in this invention that Lopap increases expression of extracellular proteins (ECM). More specifically, Lopap increases expression of fibronectin, tenascin, collagen, and elastin. The data of Example 7 demonstrates that Lopap increases expression of Type III collagen in Experimental Group 1, Group 2, and Group 3.

Muscle is contractile tissue of the body whose function is to produce force and cause (1) locomotion or (2) movement within internal organs. Muscle movement within organs, disregulated or extensive over time, causes organs to malfunction (e.g. eye myopia, spasms) or age (e.g. skin structure, heart failure). Current approaches to treat organ disorders related to disregulated or extensive muscle use, includes the use of muscle relaxants (for examples, see Scrips Reports, PJB Publications Ltd. Surrey, UK, 2000)

Nitric oxide and prostaglandin $I_2$ (prostacycline) are important signaling molecules in mammals, and they possess several biological activities, including causing relaxation of muscle tissue. It was determined in this invention that Lopap increases expression of nitric oxide and prostaglandin $I_2$ in HUVECs (see Examples) and hence, can be used to treat disorders caused by disregulated or extensive muscle use. In one embodiment, nitric oxide and prostaglandin $I_2$ can be used to treat disorders associated with aging, e.g. heart failure or skin structure such as wrinkles. The popular cosmetic drug Botox is a muscle relaxant, and it is contemplated that Lopap has the same applications and uses. In another embodiment, nitric oxide and prostaglandin $I_2$ can be used to treat eye myopia or muscle spasms.

Nitric oxide is being used in the treatment of other disorders, including hypertension, sexual dysfunction (e.g mechanism of alkyl nitrite) and erectile dysfunction. Prostaglandin $I_2$ is being used in the treatment of other disorders, including hypertension and ulcers. In another embodiment, Lopap can be used to treat diseases treatable by nitric oxide or prostaglandin $I_2$, including hypertension, sexual dysfunction, erectile dysfunction, and ulcers.

Methods of reducing or repairing tissue degeneration are also important methods for reducing cell death or degeneration.

3. Lopap and rLopap

Figure 2:
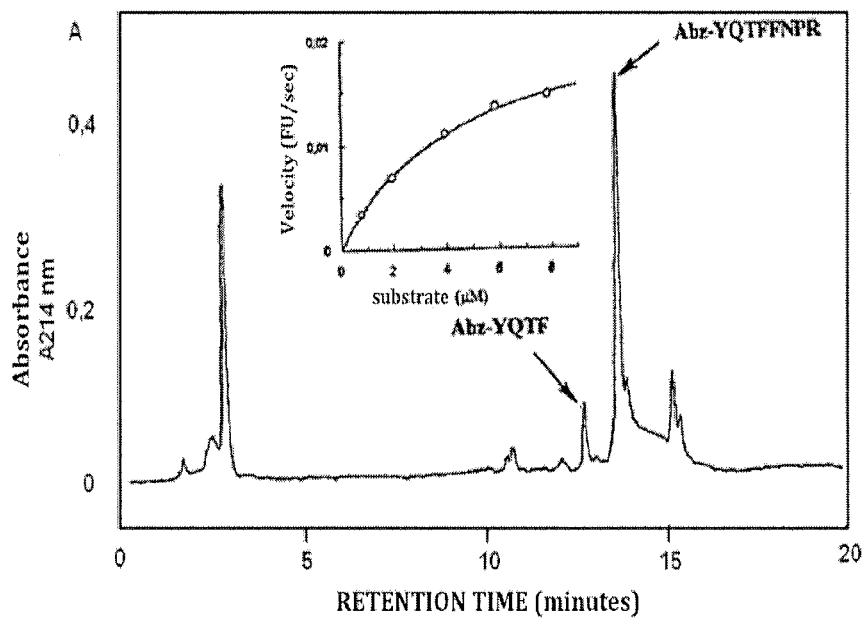
FIG. 2 shows the protease activity of the protein Lopap on the substrate Abz-YQTFFNPRTFGSQ-EDDnp (SEQ ID NO: 9) (deduced from the prothrombin molecule), as determined by reverse phase chromatography.

The naturally-occurring Lopap protein is a prothrombin activating protease from *Lonomia oblique*, which can be purified as presented in FIG. 1, comprising a step of gel filtration chromatography and two steps of reverse phase chromatography, resulting in a major band of about 69 kDa molecular weight, and may have at least one activity corresponding to FIG. 2, obtained by analysis of the protein on the substrate Abz-YQTFFNPRTFGSQ-EDDnp (SEQ ID NO: 9) (deduced from prothrombin).

The term "functional form" of the Lopap protein refers to any form of Lopap protein that retains at least one therapeutic use of the naturally-occurring protein. Examples of desired therapeutic uses include reduction of cell death, reduction of cell or tissue degeneration, repair of tissue, expression of extracellular matrix proteins, expression of nitric oxide, or expression of prostaglandin $I_2$. For the purposes of this invention, a functional form of Lopap includes, but is not limited to, the naturally-occurring Lopap, rLopap, and/or a functional derivative of any of these forms of the Lopap protein.

The term "rLopap" refers to a Lopap protein (SEQ ID NO: 1) derived from a recombinant DNA sequence encoding the Lopap protein (Brazilian patent document PI 0403882).

Unless otherwise explicitly specified in this application, any reference to "Lopap" should be construed as a reference to the naturally-occurring Lopap, the functional form of Lopap, rLopap (SEQ ID NO: 1), and/or a functional derivative of any of these forms of Lopap.

The term "derivative" refers to a protein derived or obtained from Lopap that retains at least one therapeutic use of Lopap. Examples of therapeutic uses include reduction of cell death, reduction of cell or tissue degeneration, repair of tissue, expression of extracellular matrix proteins, expression of nitric oxide, or expression of prostaglandin $I_2$. Derivatives may be produced by techniques known in the art, including deletions or additions or substitutions of amino acids, or other chemical modifications that will not affect the ability of the derivative to provide a therapeutically beneficial effect to the treated cell or tissue.

A derivative may also result from the cleavage of the parent molecule, cyclisation and/or coupling with one or more additional moieties that improve Volubility, altering the lipophilic characteristics to enhance uptake by cells, altering stability or biological half-life, decreasing cellular toxicity, or, in particular in vitro or ex vivo applications, acting as a label for subsequent detection, or the like. Moreover, a derivative may result from post-translational or post-synthesis modification such as the attachment of carbohydrate moieties or chemical reaction(s) resulting in chemical modification(s) such as alkylation or acetylation of amino acid residues or other changes involving the formation of chemical bonds.

Derivatives may also result from chemical modifications such as coupling, acetylation, acylation, ADP-ribosylation, amidation, covalent attachment of other functional moiety, covalent attachment of lipid or lipid derivative, covalent attachment of phosphotidylinositol, cross-linking, icyclization, disulfide bond formation, demethylation, formation of covalent cross-links, formulation, gamma-carboxylation, glycosylation, glycophosphatidylinositol (GPI) anchor formation, hydroxylation, iodination, methylation, myristoylation, oxidation, pegylation, proteolytic processing, phosphorylation, prenylation, racemization, selenoylation, sulfation, transfer RNA mediated addition of amino acids to proteins such as arginylation, and ubiquitination. For instance, Creighton, Proteins-Structure and Molecular Properties, 2nd Ed., W. H. Freeman and Company, New York (1993); Johnson, Post Translational Covalent Modification of Proteins, Academic Press, New York, (1983); Seifter et al., *Meth. Enzymol.* 182:626-646 (1990); Rattan et al., *Ann. N.Y. Acad. Sci.* 663:48-62 (1992); U.S. Pat. No. 5,876,969; EP 0413622; and U.S. Pat. No. 5,766,883).

In another embodiment, the invention pertains to using nucleic acids encoding Lopap. The nucleic acids can be RNA or DNA. In a preferred embodiment, the nucleic acid encodes the naturally-occurring Lopap or rLopap or the functional form of Lopap. In a more preferred embodiment, the nucleic acid encodes a cDNA encoding Lopap (SEQ ID NO: 2) or a functional derivative.

In one embodiment, the Lopap nucleic acid is contained or associated with an expression vector (e.g. recombinant rekoviruses, adenovirus, adeno-associated virus, herpes simplex virus-1, or recombinant bacterial or eukaryotic plasmids, or cosmid). Viral vectors can be transfect cells directly, and plasmids can transfect cells with use of cationic liposomes (lipofectin), polylysine conjugates, gramacidin S. artificial viral envelopes, direct injection, electroporation, or $CaPO_4$. In another embodiment, the Lopap nucleic acid is contained or associated with a cell (e.g. transfected) or tissue or animal or plant (e.g. transgenic). The cell or tissue or animal or plant that contains and expresses the Lopap nucleic acid—contained or not in an expression vector—can be used as a source for Lopap protein, and the expressed protein can be isolated using standard techniques.

The term "substantially identical", in the context of two or more peptides, or two or more nucleic acids, refers to two or more sequences or subsequences having at least 60%, preferably at least 80%, more preferably at least 85% 90%, 95% or higher identity between amino acid or nucleotide residues, in comparison or aligned for maximum correspondence, as measured by using a sequence comparison algorithm, such as BLAST algorithm (Altschul et al, *J. Mol. Biol.* 215: 403-410 (1990)), the local homology algorithm by Smith & Waterman, *Adv. Appl. Math.* 2: 482 (1981), the homology alignment algorithm by Needleman & Wunsch, *J. Mol. Biol.* 48: 443 (1970), by similarity search by the Pearson & Lipman method, *Proc. Natl. Acad. Sci. U.S.A.* 85: 2444 (1988), by computerized implementation of said algorithms (GAP, BESTFIT, FASTA and TFASTA in the Wisconsing Genetics Software Package, Genetics Computer Group, 575 Science Dr., Madison, Wis.).

In another embodiment, the invention pertains to polypeptides that are substantially identical to Lopap. In a preferred embodiment, the polypeptides are substantially identical to the naturally-occurring Lopap or the functional form of Lopap or the functional derivative of Lopap. In a more preferred embodiment, the polypeptides are substantially identical to rLopap (SEQ ID NO: 1).

In another embodiment, the invention pertains to nucleic acids that are substantially identical to the nucleic acids that encode Lopap. In a preferred embodiment, the nucleic acids are substantially identical to the nucleic acids that encode the naturally-occurring Lopap or the functional form of Lopap or rLopap or the functional derivative of Lopap. In a more preferred embodiment, the nucleic acids are substantially identical to SEQ ID NO: 2.

Lopap can be tested for biological activity (e.g., cell viability, stimulation of cellular matrix proteins) both in vitro or in vivo. Testing can be performed as described in the examples section, or according to methods well known in the art, such as DNA Fragmentation.

Lopap and rLopap can be administered alone, or in addition with an agent to obtain a synergistic effect, e.g, a combination therapy. Examples of agents that can improve cell viability include growth factors (e.g. epidermal growth factor (EGF) and basic fibroblast growth factor (bFGF)) and antioxidants (e.g. sodium metabisulfite, sodium thiosulfate, acetylcysteine, butylated hydroxyanisole, and butylated hydroxytoluene). Examples of agents that can repair tissue include protease inhibitors (e.g. inhibitors to matrix metalloproteases, e.g. hydroxamic acid), and agents to stimulate or replace ECM (e.g. amelogenin and ECM proteins and precursors). Other examples include agents to suppress the specific disorder being treated (e.g. immunosupressants for inflammatory disorders).

4. Compositions and Formulations

In one aspect, this invention provides methods and compositions that include a prophylactically and therapeutically effective amount of at least one polypeptide or nucleic acid which is preferably at least 60%, preferably at least 80%, more preferably at least 85%, 90%, even more preferably at least 95% identical to Lopap or rLopap.

In another aspect, this invention provides methods and compositions to reduce cell death or degeneration, or to reduce or repair tissue degeneration. In general, the methods involve providing an effective amount of Lopap sufficient to modulate cell death or degeneration, or tissue degeneration.

In one embodiment of the invention, the cells or tissues to be treated are undergoing death or degeneration caused by natural or non-natural disorders, such as wound, disease, aging, or caused by external agents.

Compositions—including pharmaceutical compositions and cosmetic compositions—containing Lopap—may be prepared by conventional techniques (e.g. Remington: The Science and Practice of Pharmacy, 19th Ed., 1995) or the techniques described below. The compositions may appear in conventional forms, e.g., capsules, tablets, aerosols, solutions, suspensions or topical applications.

Typical compositions include Lopap associated with a pharmaceutically or cosmetically acceptable excipient, which may be a carrier or diluent or combination thereof, or enclosed within a carrier in the form of an ampule, capsule, sachet, paper or other container. Conventional techniques for the preparation of compositions may be used. When the carrier serves as a diluent, it may be solid, semi-solid, or liquid, which acts as a vehicle, excipient, or medium for the polypeptide. Lopap can be adsorbed on a granular solid container, e.g., in a sachet. Examples of carriers are water, salt solutions, alcohols, polyethylene glycols, polyhydroxyethoxylated castor oil, peanut oil, olive oil, lactose, terra alba, sucrose, cyclodextrin, microspheres, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Other examples are buffers (e.g. phosphate, succinate, citrate, acetate, organic substances or their salts); antioxidants (e.g. ascorbic acid); low molecular weight peptides (<10 amino acids) (e.g. polyarginine or tripeptides); proteins (e.g. serum albumin or immunoglobulins); hydrophilic polymers (e.g. polyvinylpyrrolidone); amino acids (e.g. glycine, glutamic acid, aspartic acid, arginine); monosaccharides, disaccharides; carbohydrates including cellulose and its derivatives; glucose, mannose, or dextrins; chelating agents (e.g. EDTA); sugar alcohols (e.g. mannitol or sorbitol); counterions (e.g. sodium); surfactants (e.g. polysorbates); poloxamers; and polyethyelene glycols.

The compositions may include additives, adjuvants, auxiliary agents, emulsifying agents, suspending agents, buffers, salt for osmotic pressure, preserving agents, stabilizers, thickeners, wetting agents, coloring or sweetening or flavoring agents. The compositions may be formulated to provide quick, sustained, or delayed release of Lopap by employing procedures known in the art.

The route of administration may be any route which transports Lopap to the desired site, such as oral, nasal, pulmonary, transdermal or parenteral, e.g., rectal, depot, subcutaneous, intravenous, intraurethral, intramuscular, intranasal, ophthalmic solution or an ointment—the topical route being preferred.

To prepare topical formulations, Lopap is placed in a dermatological vehicle as is known in the art. The amount of Lopap to be administered and Lopap's concentration in the formulation depend upon the vehicle, delivery system or device selected, the clinical condition of the patient, the side effects and the stability of Lopap in the formulation. The physician selects the appropriate (1) preparation, (2) concentration of Lopap, and (3) amount of formulation to be administered, depending upon clinical experience with the patient or similar patients. The topical formulations may be in the form of powders, ointments, gels, creams, adhesives and the like.

For nasal administration, Lopap may be dissolved or suspended in a liquid carrier for aerosol application. The carrier may contain additives such as solubilizing agents, e.g., propylene glycol, surfactants, absorption enhancers such as lecithin (phosphatidylcholine) or cyclodextrin, or preservatives such as parabens.

For ophthalmic formulations, see Mitra, Ophthalmic Drug Delivery Systems, Marcel Delker, New York, N.Y. (1993); and Iavener, Ocular Pharmacology, C.V. Mosby Co., St. Louis (1983).

For oral administration, solid or fluid doses can be prepared. Solid doses of Lopap (e.g. tablets) can include conventional ingredients such as talc, magnesium stearate, dicalcium phosphate, magnesium aluminum silicate, calcium sulfate, starch, lactose, acacia, methylcellulose, and functionally similar materials as diluents or carriers. Capsules can include Lopap plus an inert diluent in a hard gelatin capsule. Soft gelatin capsules can include a slurry of Lopap with vegetable oil, light liquid petrolatum or other inert oil. Fluid doses in the form of syrups, elixirs and suspensions can be prepared. Lopap can be dissolved in an aqueous vehicle with flavoring agents and preservatives to form a syrup. An elixir can be prepared using a hydroalcoholic vehicle (e.g. ethanol) with flavoring agents. Suspensions can be prepared with aid of a suspending agent (e.g. acacia, tragacanth, methylcellulose and the like).

Appropriate formulations for parenteral use are known to the practitioner of ordinary skill, such as injectable solutions or suspensions. Lopap is prepared in an aqueous solution in a concentration from about 1 to about 500 mg/ml. More typically, the concentration is from about 10 to 60 mg/ml or about 20 mg/ml. Concentrations below 1 mg/ml may be necessary depending on solubility and potency. The formulation—sterile—is suitable for various topical or parenteral routes, including intravenous, intradermal, intramuscular, intravascular, and subcutaneous (including continuos and semi-continuos infusion). Examples for injectable formulations are water, various salines, organic or inorganic salt solutions, Ringer's solution, dextrose solution, and Hank's solution.

Excipients can be included in the composition. Examples include cosolvents, surfactants, oils, humectants, emollients, preservatives, stabilizers and antioxidants. Pharmacologically acceptable buffers may be used, e.g., tris or phosphate. Effective amounts of diluents, additives, and excipients are those effective to obtain a pharmaceutically acceptable formulation in terms of solubility, biological activity, etc.

Lopap may be incorporated into a microsphere. Materials suitable for the preparation of microspheres include albumin, agar, alginate, chitosan, starch, hydroxyethyl starch, ovalbumin, agarose, dextran, hyaluronic acid, gelatin, collagen, and casein. The microspheres can be produced by various processes known to the person skilled in the art, such as a spray drying process or an emulsification process. The microspheres can be hardened by well-known cross-linking procedures such as heat treatment or using chemical cross-linking agents.

Slow or extended-release delivery systems, including biopolymers (biological-based systems), liposomes, colloids, resins, glyceryl monostearate, glyceryl distearate, wax, and other polymeric delivery systems or compartmentalized reservoirs, can be used with Lopap to provide a continuous or long term source of the protein. The systems also include semipermeable polymer matrices in the form of molded articles, such as films or microcapsules. Examples of polymer matrixes include polylactides (U.S. Pat. No. 3,773,919 and EP58481), copolymers of L-glutamic acid, and gamma-ethyl-L-glutamate (EP 133, 988). The matrix material is chosen based on biocompatibility, biodegradability, mechanical properties, aesthetics, and interphase properties. A sequestering agent may be useful, as carboxymethyl cellulose, to prevent dissociation of matrix polypeptide compositions.

Slow or extended release systems are useful for compositions for delivery via topical, intraocular, oral, and parenteral routes.

Lopap can also be administered in combination with an intervention procedure, such as placement of a shunt, stent, synthetic or natural excision grafts, catheter, valve, or other implantable devices.

Lopap can also be administered using a variety of articles in shape of a medical device. Examples of medical devices include wound closure devices (e.g. sutures, staples, adhesives) tissue repair devices (e.g. meshes such as o meshes for hernia repair), prosthetic devices (e.g., internal bone fixation devices, physical barriers for guided bone registeration, stems, valves, electrodes), tissue engineering devices (e.g. for use with a blood vessel, skin, a bone, cartilage, a liver), controlled drug delivery systems (e.g. microcapsules, ion-exchange resins), wound coverings, or wound fillers (e.g., alginate dressings, chitosan powders). In some embodiments, the device is a transcutaneous medical device (e.g. a catheter, a pin, an implant) which can include coated or embedded with Lopap. In some embodiments, the device is inform of a patch (e.g. a patch with an adhesive layer adhering to the skin, such as a transdermal patch).

The dose or "effective amount" of Lopap depends on the protein(s) or nucleic acid(s) used, the subject being treated (e.g. cells or tissue or patient), the condition being treated, the method of administration, the site of release, the side effects of the treatment, the scheme of administration, and other factors known by experts in the art. (For treatment of patients, the patient and his medical history should be considered.) The dose or effective amount should prevent or ameliorate symptoms of the disorder without producing unacceptable toxicity. A parenteral, oral, and topical dose can contain from 0.1 µg to 500 mg (preferably about 0.1 µg to 10 mg and more preferably 0.1 µg to 1 mg) of the polypeptide(s) per kg of body weight per day. An intranasal dose can contain 1-400 mg, e.g., 10 to 200 mg per person.

The method of use (treatment) can involve daily administration of Lopap (e.g., once to twice to continuos) for a specified number of days (e.g., 2 days, 3 days, 4 days, 7 days, 14 days, 21 days, one month, three months, six months or longer).

Lopap can be tested for biological activity (e.g., cell viability, stimulation of cellular matrix proteins) both in vitro or in vivo. Testing can be performed as described in the examples section, or according to methods well known in the art, such as DNA Fragmentation.

Compositions, e.g. cosmetic compositions, may include humectants (e.g. glycerol); glycols (e.g. ethylene glycol, propylene glycol); emulsifiers, such as $C_1$-$C_5$ alcohols, optionally partially esterified poly-hydric alcohols with fatty acids with $C_{12}$-$C_{24}$ long chains, such as glycerol monostearate, isopropyl myristate, fatty acid ester of sugar alcohols, e.g. monoester of fatty acid of sorbitan, polyoxyalkylated derivatives, ester of fatty acid of polyethoxyethylene, cholesterol, estearyl cetyl alcohol, fatty alcohols of cotton and synthetic surfactants with low HLB value; rheology modifiers (e.g., carbopol or natural or synthetic polymers), low viscosity paraffins, emollient alcohol esters, triglycerides, lypophilic substances (e.g. isopropyl miristate); pH regulators (e.g. TEA), carbonates or phosphates; chelating agents, (e.g. EDTA and its salts), and/or preserving agents. Compositions, e.g. cosmetic compositions, may contain substances with UV filter properties, pigments or coloring agents, vitamins, essences, perfumes, cosmetic bases, and other formulations and adjuvants used in compositions for topical application.

The nucleic acids encoding Lopap can be incorporated in expression vectors and used in a cell therapy or gene therapy protocols to treat disorders. The nucleic acid can be contained or associated with an expression vector (viral or bacterial or derivative thereof). Viral vectors can transfect cells directly, and plasmids can transfect cells with use of cationic liposomes, polylysine conjugates, gramacidin S. artificial viral envelopes, direct injection, or $CaPO_4$. The expression vectors or transfected cells can be introduced into a tissue or patient by methods known in the art, including intravenous injection, or by catheter (U.S. Pat. No. 5,328,470) or by stereotactic injection (e.g. Chen, et al., (1994) PNAS 91: 3054-3057). Cells can also be introduced by implantation.

5. Uses of Lopap and Compositions

The invention relates to polypeptides or nucleic acids substantially identical to Lopap, pharmaceutical and cosmetic compositions containing them, methods for preparing the compositions, and their use as medicaments. In one aspect, the invention pertains to using Lopap for treatment of disorders associated with cell death or degeneration, or tissue degeneration. More specifically, the Lopap and Lopap compositions can be used in treatment of wounds, disease, aging, or disorder causing external agents.

Lopap can be use to treat disorders associated with cell death, such as bacterial and viral infection, e.g., human immunodeficiency virus. Several neurological diseases are characterized by loss of neurons, and Lopap can be used in the treatment of these disorders, such as Alzheimer's disease, Parkinson's disease, amyotrophic lateral sclerosis (ALS) retinitis pigmentosa, spinal muscular atrophy, and various forms of cerebellar degeneration. Several hematologic diseases are associated with a decreased production of blood cells, and Lopap can be used in the treatment of these disorders, such as anemia associated with chronic disease, aplastic anemia, chronic neutropenia, and the myelodysplastic syndromes. Some of these disorders, e.g. myelodysplastic syndrome and some aplastic anemia, are associated with cell death in the bone marrow, which may result from programmed cell death, deficiencies in stromal cells or hematopoietic survival factors, or mediators from immune responses. Inflammatory disorders, such as graft rejection, autoimmunity, and severe immune responses (e.g. sepsis), are associated with organ-specific and/or systemic cell death. Myocardial infarctions and stroke are associated with cell death within the central area of ischemia, resulting from the acute loss of blood flow. Both disorders are also associated with cell death in the area outside the central ischemic zone, which occurs more slowly and often involves apoptosis. Lopap can be used to treat myocardial infarction, stroke, and other disorders associated with cell death or degeneration.

In one embodiment, the patient has been diagnosed with a disorder of cell death or degeneration, or tissue degeneration. The method further includes administering to the patient a pharmaceutically effective amount of Lopap that reduces the symptoms of the disorder. In some embodiments, Lopap is contacted directly with the cell or tissue with the disorder. The method further includes a test for the disorder after administering the Lopap to the patient. In some embodiments, the test comprises evaluating the viability or growth of cells or tissues affected by the disorder. In other embodiments, the test comprises evaluating secondary effects associated with the disorder, such as measures known in the art for neurological, hematologic, or cardiovascular function.

The term "patient" refers to any living organism in which an immune response is elicited. The term subject includes, but is not limited to, humans; non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

In another aspect, Lopap can be used in vivo or in vitro to improve viability of cells. In vitro use includes cell culture methods to propagate cells and methods to manipulate cells. Various cell types—prokaryotes and eukaryotes—can be treated with Lopap, such as animal, plant, yeast and mold, insect, and bacterial cells. Contemplated applications include cell culture for tissue engineering and stem cell work, and industrial applications. In a further aspect, Lopap can be used to improve the viability of cells in biotechnology processes, for example, cell methods for the production of molecules (e.g. organic, inorganic, and macromolecule), and cell methods to alter or degrade molecules. In one embodiment, Lopap can be added to culture medium or bodily fluids that will transport Lopap to the disordered cells.

In another aspect, Lopap can be used in vivo or in vitro to reduce or repair degeneration of tissues. The use includes methods of tissue culture, manipulation, and growth (including use of tissue-forming molds). Various cells types—prokayotes and eukaryotes—can be treated with Lopap, such as animal, plant, yeast and mold, insect, and bacterial cells. Contemplated applications include tissues for industrial applications, and tissue engineering. In one embodiment, Lopap can be added to culture medium or bodily fluids that will transport Lopap to the disordered tissue; or Lopap can be applied directly to the disordered tissue.

Lopap can be used to repair or grow the extracellular matrix. In one embodiment, Lopap can be used to repair or grow fibronectin. In a second embodiment, Lopap can be used to repair or grow tenascin. In a third embodiment, Lopap can be used to repair or grow collagen. And in a fourth embodiment, Lopap can be used to repair or grow elastin.

Lopap can be used to grow tissue. In one embodiment, Lopap can be used to grow tissue in a patient. In a second embodiment, Lopap can be used to grow tissue in vitro. In a third embodiment, Lopap can be used to grow tissue with one or more agents that cause tissue growth. And in a fourth embodiment, Lopap can be used to grow epithelial tissue.

Lopap can be use to treat disorders associated with the extracellular matrix, for example, disorders associated with matrix metalloprotease (MMP) activity, such as ulcers, asthma, acute respiratory distress syndrome, skin disease and wounds, skin aging and wrinkles, keratoconus, restenosis, osteo- and rheumatoid arthritis, joint disease and wounds, bone disease and wounds, invasiveness, hypovolemic shock, periodontal disease, epidennolysis bullosa, scleritis, atherosclerosis, multiple sclerosis, inflammatory diseases, vascular leakage syndrome, and collagenase induced disease.

In another aspect, Lopap can be used to stimulate nitric oxide and prostaglandin $I_2$, which possess several biological activities, including causing relaxation of muscle tissue. In one embodiment, Lopap can be used to treat disorders that benefit from muscle relaxation, including hypertension and erectile dysfunction. In another embodiment, Lopap can be used to treat disorders caused by dysregulated or extensive muscle use, such as myopia, spasms, aging, skin aging, and heart failure). In another another embodiment, Lopap can be used to treat disorders treatable by nitric oxide, such as sexual dysfunction (e.g mechanism of alkyl nitrite). In another embodiment, Lopap can be used to treat disorders treatable by prostaglandin $I_2$, such as ulcers.

In another embodiment, based on homology with lipocalin proteins, Lopap is a transporter of hydrophobic or organic compounds important in regulating cell death or degeneration, or tissue degeneration (US20040084867; US20050069877; Flower, et al., Biochim. Biophys. Acta 1482: 9-24, 2000). In one embodiment, Lopap is a transporter of retinol, which is important in cell death or degeneration, or tissue degeneration. In another embodiment, Lopap is a transporter of lipids, which are important in cell death or degeneration, or tissue degeneration.

The invention is also illustrated by way of the examples below, which are provided as examples of the invention, with no intention to limit the scope of the invention.

EXAMPLE 1

Anti-apoptotic Effect of Lopap Culture of Endothelial Cells

HUVECs were obtained by means of digestion with collagenase, following the method by Jaffe and contributors (Jaffe, E. A. et al., *J. Clin. Invest.*, 1973; 52: 2745-2756). Cells of 1-3 passages were used in confluent and subconfluent monolayers according to the type of experiment affected. Initially, cells were cultivated in 25 or 75 $cm^2$ bottles with RPMI containing 10% fetal bovine serum (FBS). When confluent, the monolayer was detached with trypsin/EDTA and the cells were seeded over 24 well plates, as required for the experiment.

Anti-Apoptotic Effect To evaluate the anti-apoptotic activity of rLopap and the native Lopap (5 and 25 μg/ml), programmed cell death was induced by incubation of HUVECs for 48 hours in RPMI medium containing 1% FBS without (control) or in the presence of rLopap or native Lopap.

Morphologic changes and cell viability were analysed by HUVEC coloring with a mixture of fluorescent colorants linking to DNA, acridine orange (100 μg/ml) to determine the percentage of cells suffering apoptosis, and ethidium bromide to differentiate between viable and non viable cells.

The presence of apoptotic cells was evaluated by fluorescence microscopy, by using non-adherent cells and adherent cells detached with trypsin/EDTA. At least 200 cells were analysed in the experiment.

Lopap (5 μg/ml and 25 μg/ml) proved to be able to inhibit the apoptosis of endothelial cells derived from human umbilical cord (HUVECs) (Table 1) when the apoptosis was induced by reduction of fetal bovine serum (1%). Higher Lopap concentrations are able to produce more effective consequences over the anti-apoptotic activity.

TABLE 1

Anti-apoptotic action of Lopap and rLopap on HUVECs. Apoptosis was induced by reduction of FBS (1% FBS)
% OF APOPTOTIC CELLS

| Control | Lopap 5 μg/ml | Lopap 25 μg/ml | rLopap 5 μg/ml | rLopap 25 μg/ml |
|---|---|---|---|---|
| 52 ± 2 | 36 ± 4 | 24 ± 2 | 39 ± 3 | 32 ± 2 |

EXAMPLE 2

Viability

Viability analysis was made by using the MTT method. The reduction of 3-(4,5-dimethylthiazol-2-methyl)-2,5-diphenyltetrazolium bromide (MTT) by intact cells was evaluated on 96 well microplates. HUVECs were cultivated in RPMI medium supplemented with 1% fetal bovine serum and, after 48 hours of incubation with Lopap (0.15 to 20 μg/ml), the culture was washed with phosphate-buffered saline (PBS). 10 μl/well of 2.5 mg/ml MTT were added and the cells were incubated for three hours at 37° C. The reaction was interrupted by the addition of 150 μl of SDS. Absorbance values at 540 nm were determined by using an automatic microplate reader.

Figure 3:
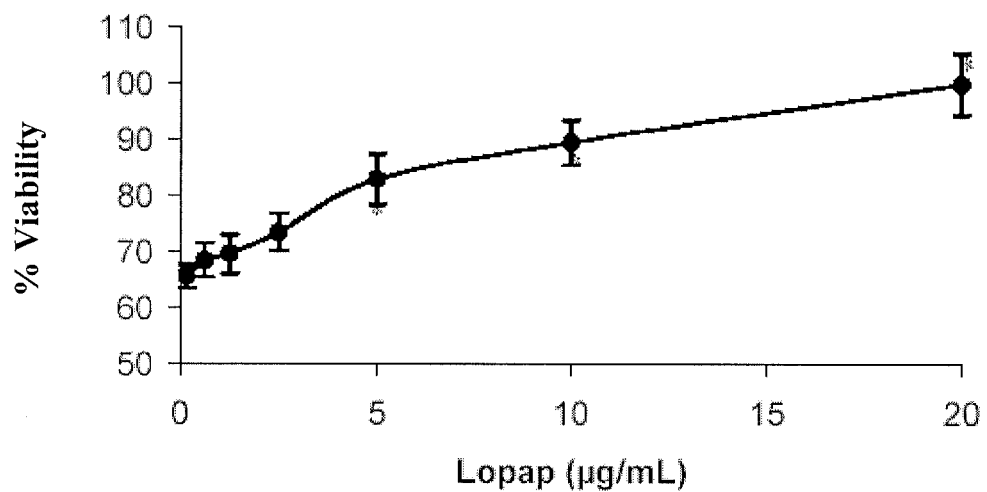
FIG. 3 shows cell viability. HUVECs ($1\times10^4$) were incubated with RPMI medium supplemented with 1% FBS without or with Lopap. An MTT assay was affected after 48 hours. The percentage of viable cells is expressed in relation to non-treated cells.

Lopap significantly improved cell viability in a concentration-dependent way (FIG. 3).

EXAMPLE 3

Production of Prostacycline

Figure 4:
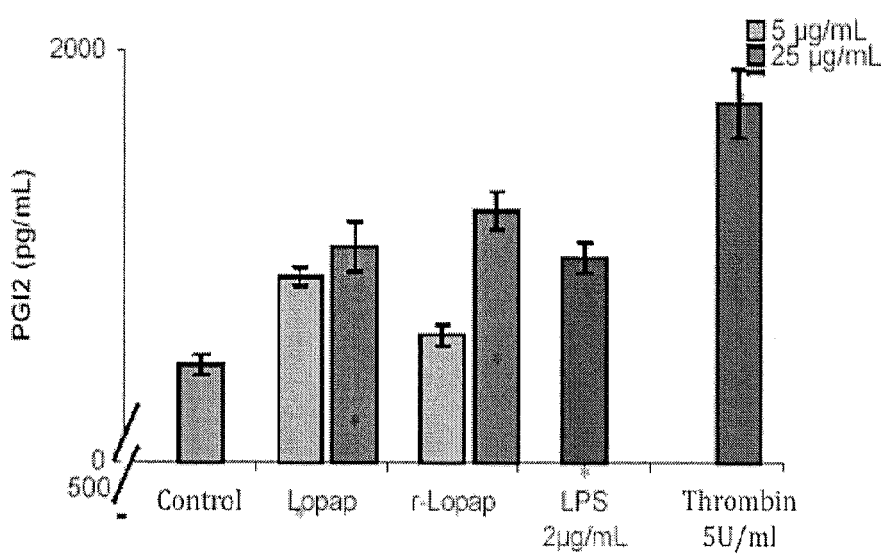
FIG. 4 shows the release of Prostaglandin $I_2$. HUVECs were incubated for one hour in RPMI 1640 culture medium in the absence or presence of metalloproteases. $PGI_2$ concentration was determined in the supernatant by the accumulation of the metabolite 6-keto-$PGF_{1\alpha}$ in the culture medium as measured by a competitive immunoenzimatic assay.

Prostacycline ($PGI_2$) production was measured by the accumulation of 6-keto-$PGF_{1\alpha}$ (a metabolite from $PGI_2$ hydrolysis) in the culture medium by ELISA after HUVEC treatment with rLopap and native Lopap. The supernatant was centrifuged at 400 xg for ten minutes at 4° C. HUVEC treatment with native Lopap for one hour (final 5 and 25 g/ml) produced a statistically significant improvement in $PGI_2$ release compared to control. rLopap (25 μg/ml) stimulated $PGI_2$ release, similar to that induced by LPS (2 μg/ml) (FIG. 4).

EXAMPLE 4

Production of Nitric Oxide

Figure 5:
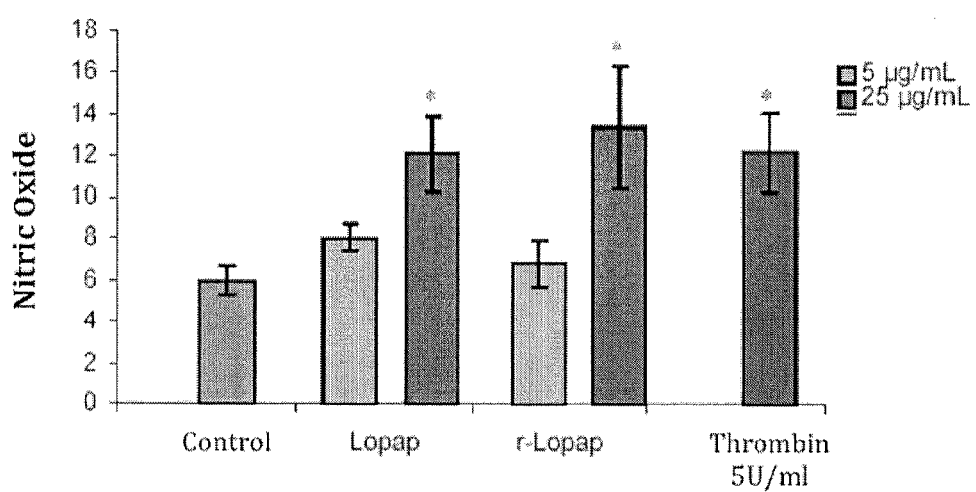
FIG. 5 shows the release of nitric oxide. HUVECs were incubated for 1 hour in HAM F12 culture medium in the absence or presence of Lopap or r-Lopap. NO concentration was determined in the supernatant after reduction of nitrate and nitrite to NO, as detected by chemiluminescence in gas phase after reaction with ozone.

Nitric oxide (NO) production was measured by combining the accumulation of nitrite and nitrate in the culture medium HAM-F12. After the treatment of HUVECs with rLopap or native Lopap (final 5 and 25 μg/ml), the supernatant was centrifuged at 400×g for ten minutes at 4° C. Nitric oxide concentration in the supernatant was determined by chemioluminescence in gaseous phase, by using a nitric oxide analyzer through the reaction between NO and ozone, after the reduction of nitrate and nitrite with $VCl_3$ saturated solution in 1 M HCl at 90° C. Nitrate concentration was calculated from a standard curve of sodium nitrate. Stimulation with native Lopap and rLopap (25 μg/ml) produced a statistically significant increase in NO release in comparison with the control, being said increase similar to the one induced by thrombin (5 UI/ml) (FIG. 5).

EXAMPLE 5

RNA Preparation (HUVECs)

RNAs as obtained presented good quality (260/280≅1.7 ratio) and 2% agarose gel analysis disclosed the presence of bands 18S and 28S, confirming the integrity of RNA as obtained.

Gene Expression in Endothelial Cells (HUVECs)

The expression of different target genes was measured by RT-PCR from confluent cultures (500,000 cells/well) in 6-well plates, where HUVECs were incubated for eight hours in RPMI medium containing 10% FBS in the absence (control) or in the presence of LOPAP 10 μg/ml, Thrombin 5 U/ml, TNF-α 5 μg/ml, or LPS 5 μg/ml, to evaluate its direct action.

Primers

Primers were designed based on a sequence of human genes (already published) to amplify proteins of interest.

TABLE 2

Sequence of primers and size of PCR products

| PRIMER | Sense | Anti-Sense |
|---|---|---|
| BCL-2 (279 bp) | 5'GAGGAAGTAGACTGATATTA3' (SEQ ID NO: 3) | 5'CCTTCCCAGAGGAAAAGCAA3' (SEQ ID NO: 4) |
| BAX (542 bp) | 5'GATGGACGGGTCCGGAGA3' (SEQ ID NO: 5) | 5'CTCAGCCCATCTTCTTCCAG3' (SEQ ID NO: 6) |
| GAPDH (996 bp) | 5'GGTGAAGGTCGGAGTCAACG3' (SEQ ID NO: 7) | 5'TCCTTGGAGGCCATGTGGGCCCT3' (SEQ ID NO: 8) |

Expression of the Constitutive Gene of GAPDH Cells (Control)

Figure 6:
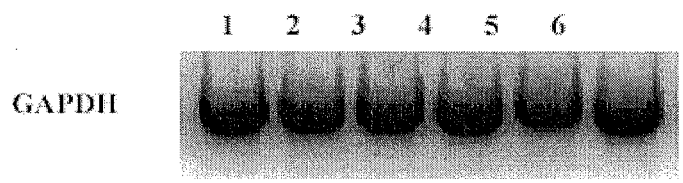
FIG. 6 presents the expression of GAPDH detected by RT-PCR in HUVECs (10% FBS), 1-control, non-stimulated cells, 2-cells stimulated with 5 U/ml Thrombin, 3-cells stimulated with 5 ng/ml TNFα, 4-cells stimulated with 5 µg/ml LPS, 5-cells stimulated with 10 µg/ml Lopap and 6-cells stimulated with 10 µg/ml rLopap.

Using RT-PCR, densitometric analysis was performed on test genes and the constitutively expressed gene, glyceraldehyde-3-phosphate dehydrogenase (GAPDH). In HUVECs, GAPDH presented homogeneous expression for all stimuli made. Electrophorectic migration of the applied fragment was 996 bp, as expected (FIG. 6).

Expression of the Gene Bcl-2 (anti-apoptotic)

Figure 7:
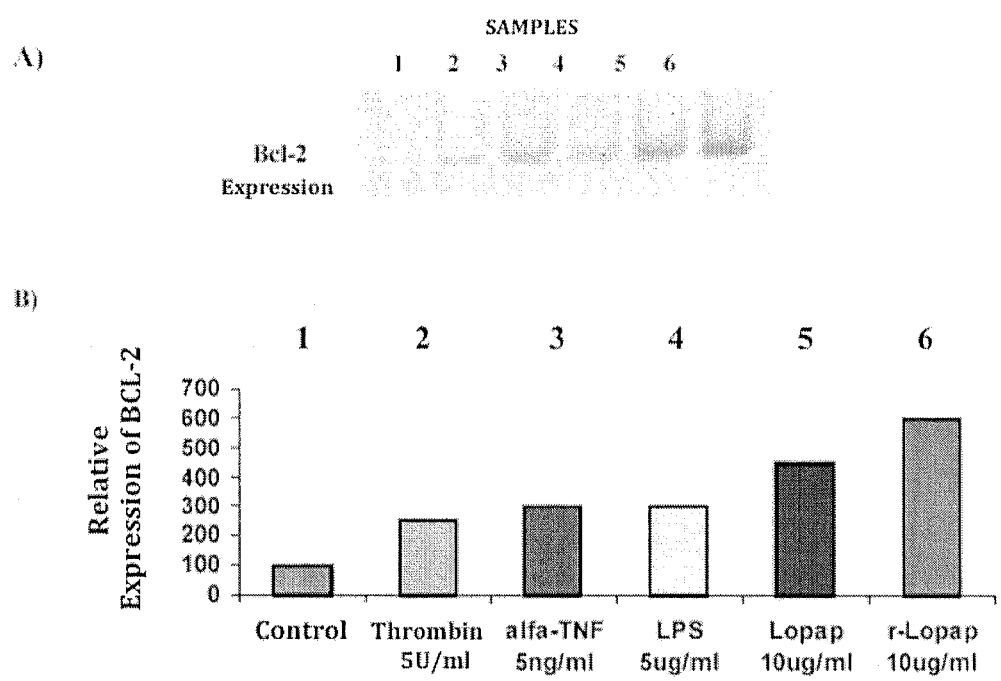
FIG. 7 presents the expression of Bcl-2 detected by RT-PCR in HUVECs (10% FBS), 1-control, non-stimulated cells, 2-cells stimulated with 5 U/ml Thrombin, 3-cells stimulated with 5 ng/ml TNFα, 4-cells stimulated with 5 µg/ml LPS, 5-cells stimulated with 10 µg/ml Lopap, and 6-cells stimulated with 10 µg/ml rLopap. Expression is calculated relative to expression of the control gene GAPDH.

Electrophorectic migration in a 2% agarose gel from the PCR reaction with primer to Bcl-2 showed the generation of 279 bp fragments as expected. HUVECs stimulated with Lopap and rLopap presented remarkable improvement in the expression of the gene Bcl-2 over the negative control and other stimuli made (FIG. 7).

Expression of the Gene Bax (pro-apoptotic)

Figure 8:
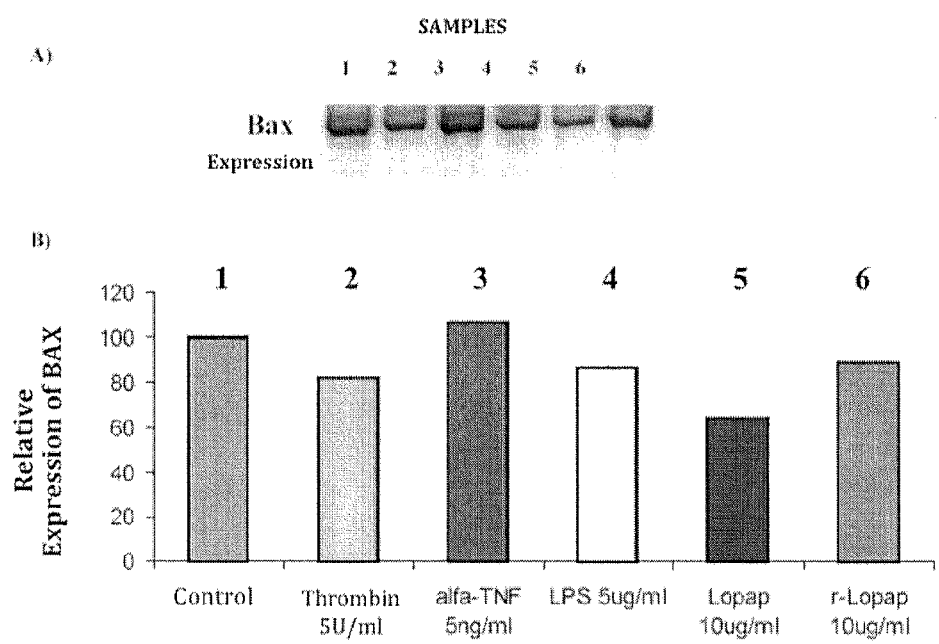
FIG. 8 presents the expression of Bax in HUVECs (10% FBS), 1-control, non-stimulated cells, 2-cells stimulated with 5 U/ml Thrombin, 3-cells stimulated with 5 ng/ml TNFα, 4-cells stimulated with 5 µg/ml LPS, 5-cells stimulated with 10 µg/ml Lopap, and 6-cells stimulated with 10 µg/ml rLopap. Expression is calculated relative to expression the control gene GAPDH.

Electrophorectic migration under 2% agarose gel from the PCR reaction with primer to Bax showed the generation of 542 bp fragments as expected. HUVECs stimulated with Lopap and rLopap presented remarkable reduction in the expression of the gene Bax; especially cells stimulated with native Lopap, over the negative control and other stimuli made (FIG. 8).

EXAMPLE 6

Action of rLopap on Human Skin Fibroblasts. Evaluation of Components in the Extracellular Matrix: Fibronectin and Tenascin Human skin fibroblasts in culture were plated over platelets in a 24-well plate and incubated with rLopap under different concentrations for seven days to evaluate the action of said protein for the production of components of the extracellular matrix (fibronectin and tenascin).

Biological Material

The assay system comprised human skin fibroblasts in culture, obtained from the fragment of normal skin from the ear lobule of five female Negro individuals, aged 15 to 40 years old.

Collection of the Biological Material

Patients were submitted to excision biopsy, after informed consentment, in a surgical room with usual asepsis and antisepsis criteria. A fragment of normal skin measuring 0.5 cm×0.5 cm was collected and immediately immersed in a sterile culture medium of Ham-F-12 with 15% FBS (fetal bovine serum) and antibiotics.

Test Plan: Control and Test Groups

The control group was constituted by fibroblasts cultured in culture medium of Ham-F-12 supplemented with 10% FBS.

Two assay groups were defined: 1) fibroblasts cultivated in culture medium plus 1 μg rLopap, and 2) fibroblasts cultivated in culture medium plus 5 μg rLopap.

Preparation of the Plate

All fibroblast samples used in the experiment consisted of the sixth subcultivation. Sterile culture plates with 24 wells were used. Fibroblasts were cultivated in sterile round plates with 13 mm diameter, and in each plate, $1 \times 10^5$ fibroblasts were plated in 1 ml culture added with FBS. After 24 hours for cell adherence, the medium was changed with new culture medium and rLopap at the final volume of 300 μl/well.

rLopap used was stored at room temperature, filtered through a 0.22 μm membrane under 1 μg/μl and 5 μg/μl concentrations.

Plates were kept at 37° C. in a $CO_2$ oven for seven days and observed at an inverted microscope.

Fixation of Plates

Plates were carefully washed 1× with 1 ml PBS. Plates were fixed for 15 minutes with 400 μl fixing agent comprising 3% paraformaldehyde and 0.2% glutaraldehyde in 0.1 M phosphate buffer pH 7.4, and washed 1× with 1 ml PBS.

Indirect Immunofluorescence

Plates were incubated for 45 minutes with 50 μl of primary monoclonal antibody—anti-cellular fibronectin or anti-human tenascin—diluted 1:100 in PBS.

Subsequently, plates were incubated for 45 minutes with 50 μl of the secondary antibody Alexa Fluor 488, diluted 1:100 in PBS. Plates were assembled in a microscopy slide with one drop of the Vectashield assembly medium with DAPI (Vector Laboratories-U.S.A.).

Evaluation of Fibronectin and Tenascin Production by Fibroblasts by Histomorphometric Analysis.

Slides, when submitted to immunofluorescence, were analysed under light and fluorescence microscope (Zeiss) with 20× objective lens and 10× eye lens and the quantitative evaluation was made with the support of an Image Analysing System.

Images obtained in 10 microscopic fields were digitalized with the support of the software, providing the possibility to share data with the text editor (Microsoft Word®) and spreadsheets (Microsoft Excel®). For a quantitative evaluation of the production of fibronectin and tenascin, fluorescent structures were marked, so to differentiate them from other structures by color contrast. The area of fibronectin and tenascin was obtained by digital densitometry, which was transformed to square micrometers ($\mu m^2$). Results obtained in each field correspond to the percentual area of positive structures, i.e. fraction of area.

Statistical Analysis

Data of area fraction for studied samples were submitted to descriptive statistics and the comparison between the groups was made by a non-parametric Kruskal-Wallis test or by ANOVA parametric test. $p<0.05$ was considered as significant.

Values were obtained from the area fraction of fibronectin and tenascin from the five samples of fibroblasts cultured over the action of rLopap (1 μg and 5 μg) and control group. These values were submitted to descriptive statistic analysis, whose results are specified on Table 3.

TABLE 3

Average and standard error for the expression (%) fibronectin and tenascin in normal human fibroblast cultures treated with 1 and 5 μg of rLopap and control group

| Treatment | n | Average | Standard Error | Max | Min |
|---|---|---|---|---|---|
| % Fibronectin rLopap (1 μg) | 50 | 46.1 | 15.1 | 72.8 | 16.8 |
| % Fibronectin rLopap (5 μg) | 50 | 24.2 | 18.4 | 61.4 | 0.1 |
| % Fibronectin Control | 50 | 19.2 | 7.4 | 38.4 | 5.1 |
| % Tenascin rLopap (1 μg) | 50 | 2.3 | 1.5 | 5.8 | 0.4 |
| % Tenascin rLopap (5 μg) | 50 | 1.7 | 1.1 | 4.8 | 0.4 |
| % Tenascin control | 50 | 0.8 | 0.4 | 2.1 | 0.1 |

Figure 9:
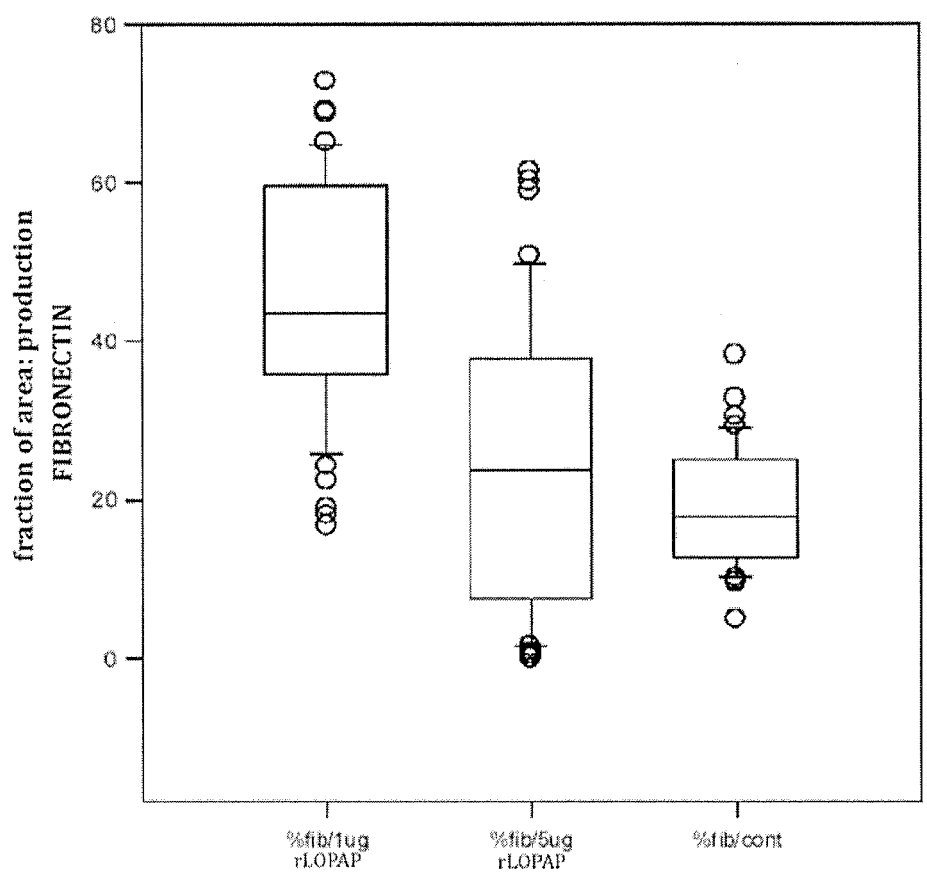
FIG. 9 shows fibronectin expression in fibroblasts untreated and treated with rLOPAP (1 and 5 µg). The x-axis is denoted % positive cells/treatment method.

The comparison between fraction values in the area of fibronectin as produced by fibroblasts grown with protein under 1 μg and 5 μg concentrations, and the control group, disclosed a statistically significant difference ($p<0.001$), showing higher production of fibronectin by fibroblasts cultivated with rLopap over the control group (FIG. 9).

Figure 10:
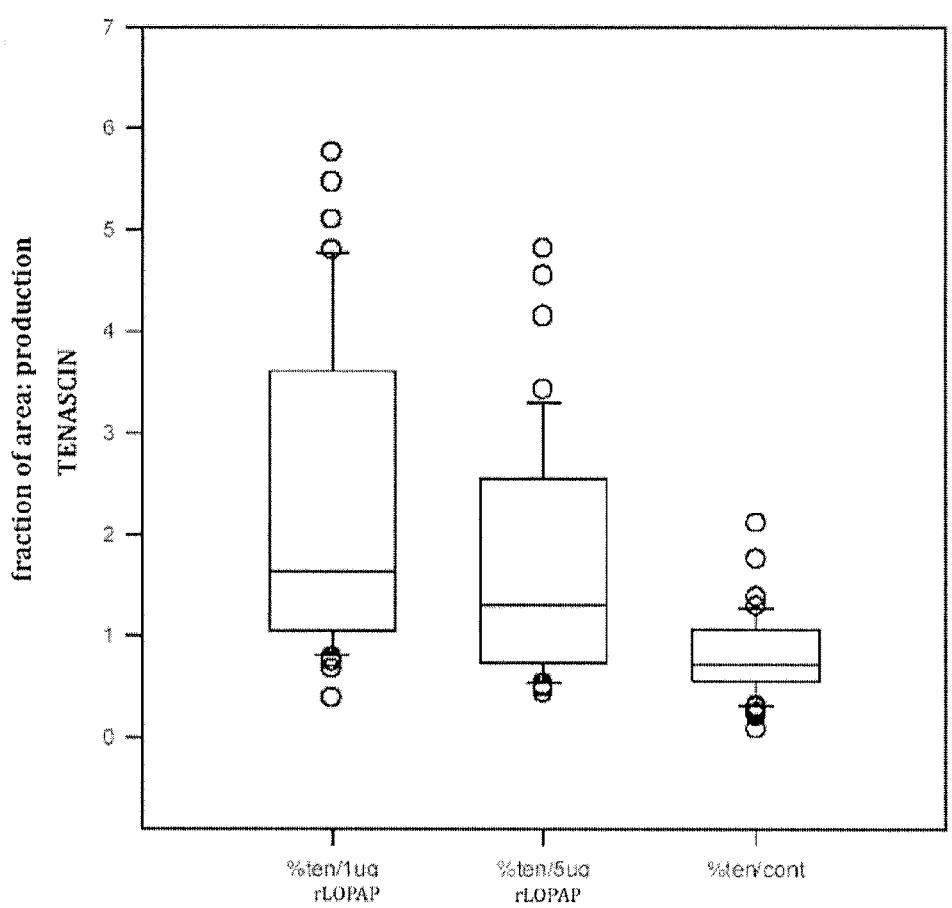
FIG. 10 shows tenascin expression in fibroblasts untreated and treated with rLOPAP (1 and 5 µg). The x-axis is denoted % positive cells/treatment method.

The comparison between fraction values in the area of tenascin as produced by fibroblasts grown with protein (1 μg and 5 μg) and the control group disclosed a statistically significant difference ($p<0.001$), showing higher production of tenascin by fibroblasts cultivated with rLopap over the control group (FIG. 10).

Figure 11:
FIG. 11 shows indirect immunofluorescence for fibronectin in: A) normal human fibroblasts (control group); B) normal human fibroblasts grown in the presence of 1 µg rLopap; C) normal human fibroblasts grown in the presence of 5 µg rLopap.

FIG. 11 shows the distribution of fibronectin on cultivated human skin fibroblasts: control group, (A) 1 μg rLopap (B) and 5 μg Lopap (C).

Figure 12:
FIG. 12 shows indirect immunofluorescence for tenascin in: A) normal human fibroblasts (control group); B) normal human fibroblasts grown in the presence of 1 µg rLopap; C) normal human fibroblasts grown in the presence of 5 µg rLopap.
Figure 13:
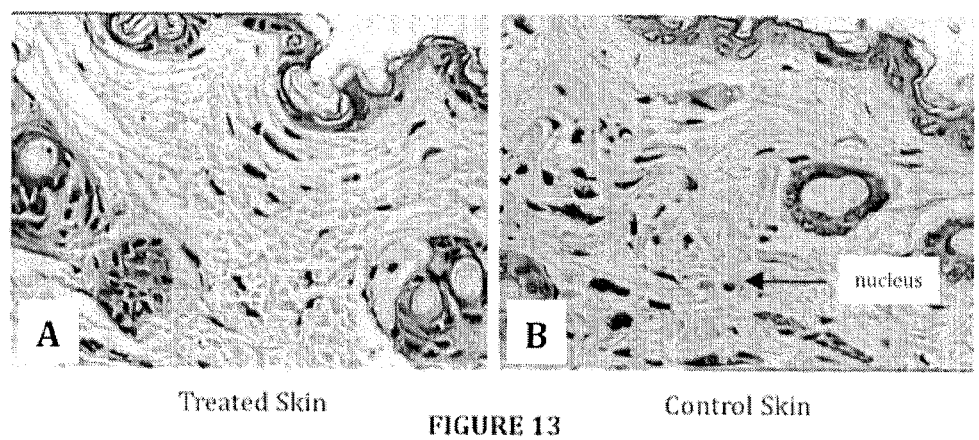
FIG. 13 shows a photomicrograph of epidermis of animals treated with rLopap, (A) treated skin and (B) control skin. The presence of similar quantity of fibroblast nuclei on the dermis is noticed.
Figure 14:
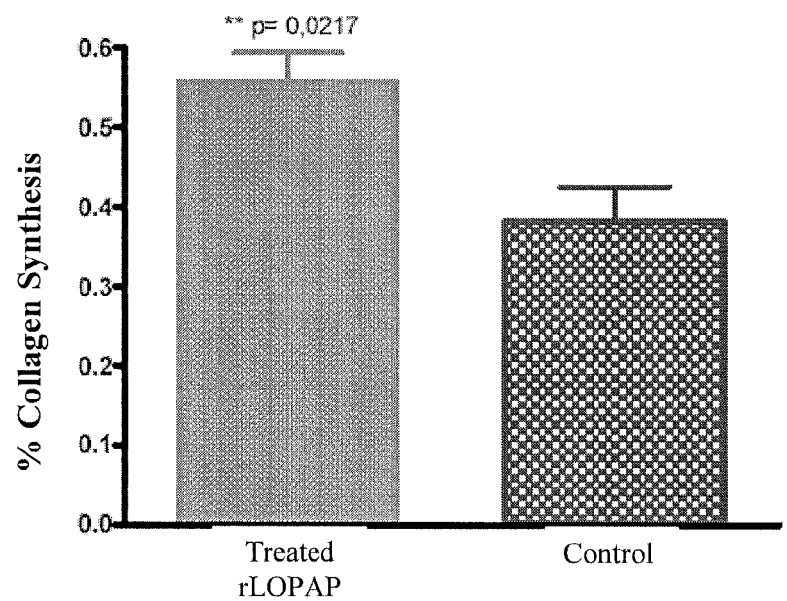
FIG. 14 shows expression of Type III collagen by control skin and Experimental Group 1 skin.
Figure 15:
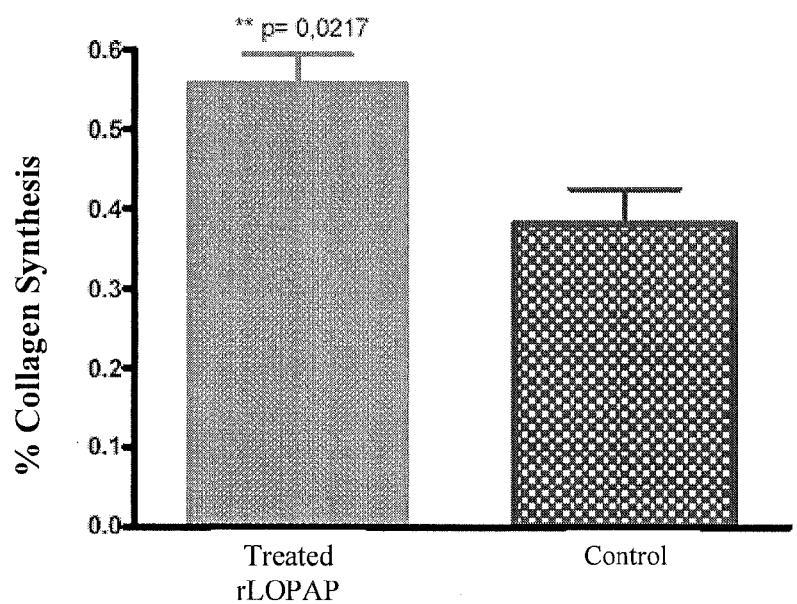
FIG. 15 shows expression of Type III collagen by control skin and Experimental Group 2 skin.
Figure 16:
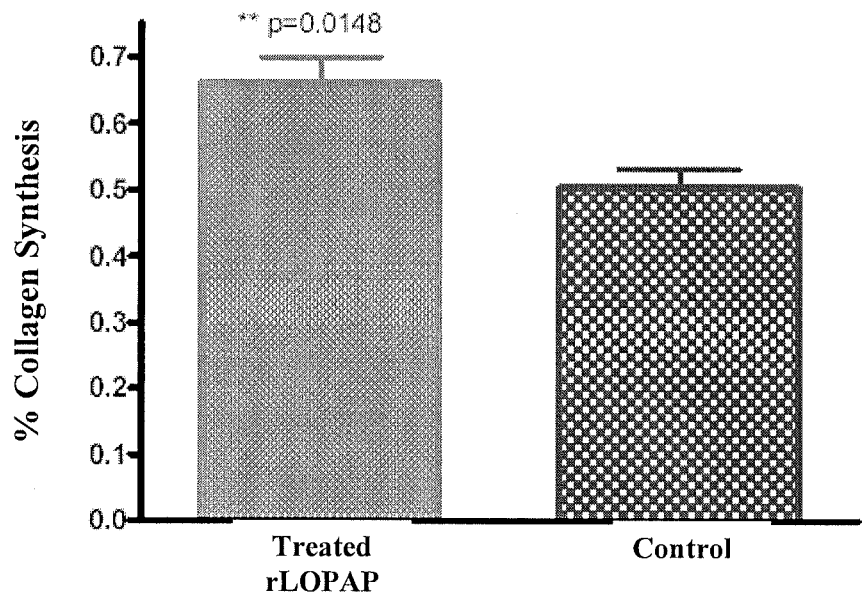
FIG. 16 shows expression of Type III collagen by control skin and Experimental Group 3 skin.
Figure 17:
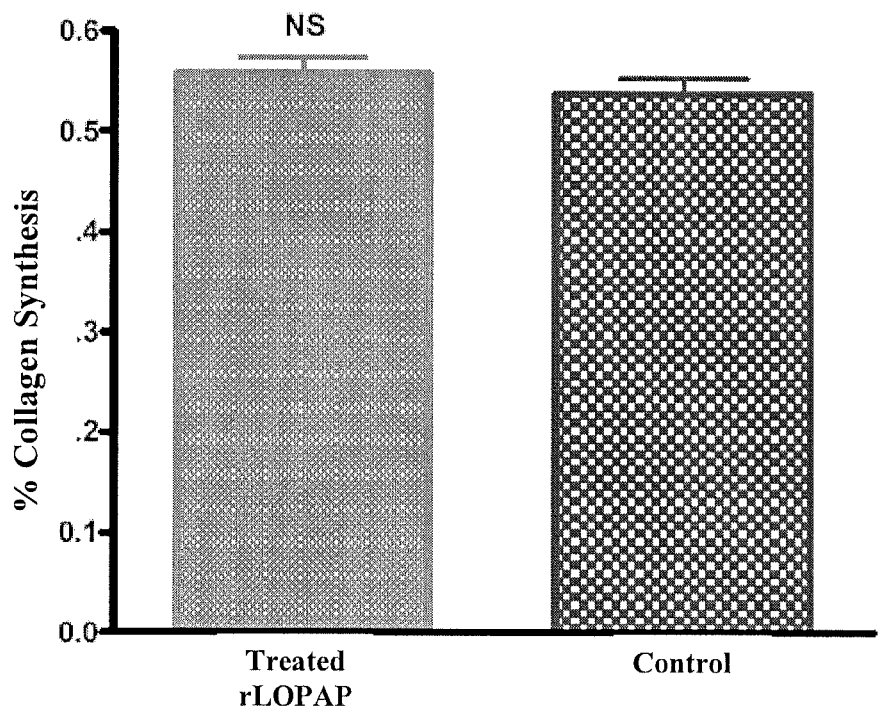
FIG. 17 shows expression of Type III collagen by control skin and Experimental Group 4 skin.
Figure 18:
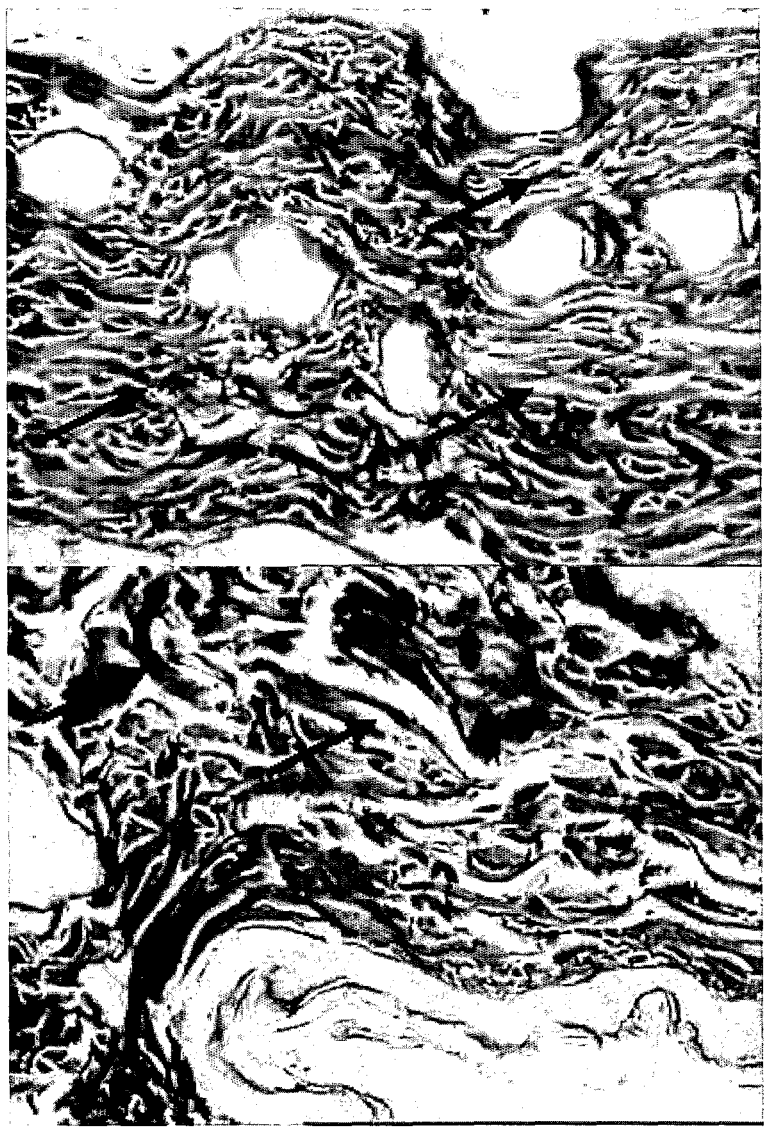
FIG. 18 shows photomicrographs of the dermis of animals treated with rLopap (340×). Dense collagen fibers (arrows) are observed.

FIG. 12 shows the distribution of tenascin on cultivated human skin fibroblasts: control group, (A) 1 μg rLopap (B) and 5 μg Lopap (C).

EXAMPLE 7

The dorsal region of mice was hair-cutted and submitted to topical treatment with rLopap jointly with adjuvants on the right side (experimental) and just with adjuvants on the left side (control).

Experimental groups were divided into:

Group 1: rLopap (0.33 mg) added to papain ointment (final proportion 5%), topical administration once per week for three times.

Group 2: rLopap (0.33 mg) diluted in 0.03 M NaCl, topical administration once per week for three times.

Group 3: rLopap (0.33 mg) diluted in 0.03 M NaCl, intradermal administration in a single dose.

Group 4: commercial ointment Vitanol-A, gel 0.025 tretinoin, topical administration once per week for three times.

Hystopathological Study

The treated region was taken off after animals were sacrificed and fixed in a buffered solution of 10% formalin with phosphate buffer. Skin samples were submitted to crosswise sections and submitted to histological routine. Samples were dehydrated in a growing series of alcohols, defatted in xylol and embedded in paraffin. Samples were then inserted in paraffin and submitted to 3 μm thick cuts in histological microtome, which were collected on glass blades. Said blades were submitted to Hematoxillin-Eosine coloring, for analysis of histological characteristics and Picrosirius coloring (Junqueira, L. C. V., et al., *Anal. Biochem.* 94: 9609-13, 1979), for collagen quantitative evaluation. Slides were examined under light microscopy, in a microscope coupled to an Image Analyser System.

Histological Characteristics

Skin of animals of all experimental groups as studied showed architecture preserved with epidermis and dermis.

Collagen III Quantification

Dermis collagen was quantified with the support of an Image Analyser Kontron 300 in skin cuts colored by Picrosirius. Five microscopic fields were evaluated with 20× objective lens and 10× eye lens. Fields were randomly chosen on the various skin fragments represented on the slide of each animal.

We noticed that the skin treated with rLopap in the different experimental groups significantly differs (p<0.001) on the ability to synthesize collagen, in comparison with non-treated skin (control) (FIGS. 13 to 18).

The invention claimed is:

1. A method of growing skin, the method comprising contacting skin, comprising fibroblasts, with a polypeptide that has at least 95% identity to the amino acid sequence of SEQ ID NO: 1, wherein the polypeptide increases expression of one or more extracellular matrix proteins in the skin, thereby growing skin.

2. The method of claim 1, wherein the method is a method of wound repair.

3. The method of claim 1, wherein the extracellular matrix protein is collagen type III.

* * * * *

UNITED STATES PATENT AND TRADEMARK OFFICE
CERTIFICATE OF CORRECTION

PATENT NO. : 8,673,840 B2
APPLICATION NO. : 12/066192
DATED : March 18, 2014
INVENTOR(S) : Ana Marisa Chudzinski-Tavassi et al.

It is certified that error appears in the above-identified patent and that said Letters Patent is hereby corrected as shown below:

On the Title Page, Item (73) (Assignees), Line 1, delete "Biolabs" and insert -- Biolab --

Signed and Sealed this
Tenth Day of June, 2014

Michelle K. Lee
*Deputy Director of the United States Patent and Trademark Office*

UNITED STATES PATENT AND TRADEMARK OFFICE
CERTIFICATE OF CORRECTION

| | | Page 1 of 1 |
|---|---|---|
| PATENT NO. | : 8,673,840 B2 | |
| APPLICATION NO. | : 12/066192 | |
| DATED | : March 18, 2014 | |
| INVENTOR(S) | : Chudzinski-Tavassi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1305 days.

Signed and Sealed this
Eleventh Day of August, 2015

Michelle K. Lee
*Director of the United States Patent and Trademark Office*

UNITED STATES PATENT AND TRADEMARK OFFICE
CERTIFICATE OF CORRECTION

PATENT NO. : 8,673,840 B2  
APPLICATION NO. : 12/066192  
DATED : March 18, 2014  
INVENTOR(S) : Chudzinski-Tavassi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1345 days.

Signed and Sealed this
Twentieth Day of October, 2015

Michelle K. Lee
*Director of the United States Patent and Trademark Office*